(12) United States Patent
Spencer

(10) Patent No.: US 10,568,750 B2
(45) Date of Patent: Feb. 25, 2020

(54) NON-SNAG PROSTHETIC FOOT AND LEG

(71) Applicant: Kenneth B. Spencer, Orderville, UT (US)

(72) Inventor: Kenneth B. Spencer, Orderville, UT (US)

(73) Assignee: Kenneth B. Spencer, Orderville, UT (US)

( * ) Notice: Subject to any disclaimer, the term of this patent is extended or adjusted under 35 U.S.C. 154(b) by 186 days.

(21) Appl. No.: 15/818,287

(22) Filed: Nov. 20, 2017

(65) Prior Publication Data

US 2019/0151119 A1    May 23, 2019

(51) Int. Cl.
| | |
|---|---|
| A61F 2/66 | (2006.01) |
| A61F 2/80 | (2006.01) |
| A61F 2/60 | (2006.01) |
| A61F 2/76 | (2006.01) |
| A61F 2/50 | (2006.01) |
| A61F 2/70 | (2006.01) |
| A61F 2/78 | (2006.01) |

(52) U.S. Cl.
CPC ............ *A61F 2/66* (2013.01); *A61F 2/601* (2013.01); *A61F 2/76* (2013.01); *A61F 2/80* (2013.01); *A61F 2002/502* (2013.01); *A61F 2002/5007* (2013.01); *A61F 2002/5021* (2013.01); *A61F 2002/5026* (2013.01); *A61F 2002/5081* (2013.01); *A61F 2002/5083* (2013.01); *A61F 2002/6614* (2013.01); *A61F 2002/704* (2013.01); *A61F 2002/7887* (2013.01)

(58) Field of Classification Search
CPC .... A61F 2/66; A61F 2/80; A61F 2/601; A61F 2/60; A61F 2002/607; A61F 2002/5007; A61F 2002/5026; A61F 2002/5081; A61F 2002/6614; A61F 2002/704; A61F 2002/7887; A61H 3/02
USPC ................................................ 623/33, 47–52
See application file for complete search history.

(56) References Cited

U.S. PATENT DOCUMENTS

| | | | | |
|---|---|---|---|---|
| 4,161,042 A * | 7/1979 | Cottingham | ............... | A61F 2/60 623/33 |
| 6,488,717 B1 * | 12/2002 | McColl | ..................... | A61F 2/60 623/35 |
| 2003/0220701 A1 * | 11/2003 | Steinbarger | ............... | A61F 2/76 623/38 |
| 2009/0036908 A1 * | 2/2009 | Zokol | .................... | A61B 17/60 606/151 |
| 2011/0240077 A1 * | 10/2011 | Doherty | .................. | A61H 3/02 135/71 |

(Continued)

*Primary Examiner* — Suba Ganesan
*Assistant Examiner* — Aren Patel
(74) *Attorney, Agent, or Firm* — Stoel Rives LLP

(57) ABSTRACT

The present disclosure illustrates a prosthetic foot that may reduce snagging on external obstacles. In some embodiments, a prosthetic foot includes a symmetric wear member that is rotatable to allow a user to alter an orientation of the symmetric wear member for even wear. A cuff may couple to the symmetric wear member, and include the proximal end comprising a receptacle with an opening having an adjustable diameter. The receptacle may be sized and shaped to receive and selectively retain the prosthesis pylon by adjusting the diameter of the opening. The prosthetic foot may further include a vertical adjustment mechanism that selectively alters a depth of the receptacle of the cuff to vertically displace the prosthesis pylon.

20 Claims, 3 Drawing Sheets

(56) References Cited

U.S. PATENT DOCUMENTS

2018/0153759 A1\* 6/2018 Clausen .................. A61H 3/02

\* cited by examiner

NON-SNAG PROSTHETIC FOOT AND LEG

TECHNICAL FIELD

The present disclosure relates generally to prosthetics. More particularly, some embodiments relate to a prosthetic foot.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
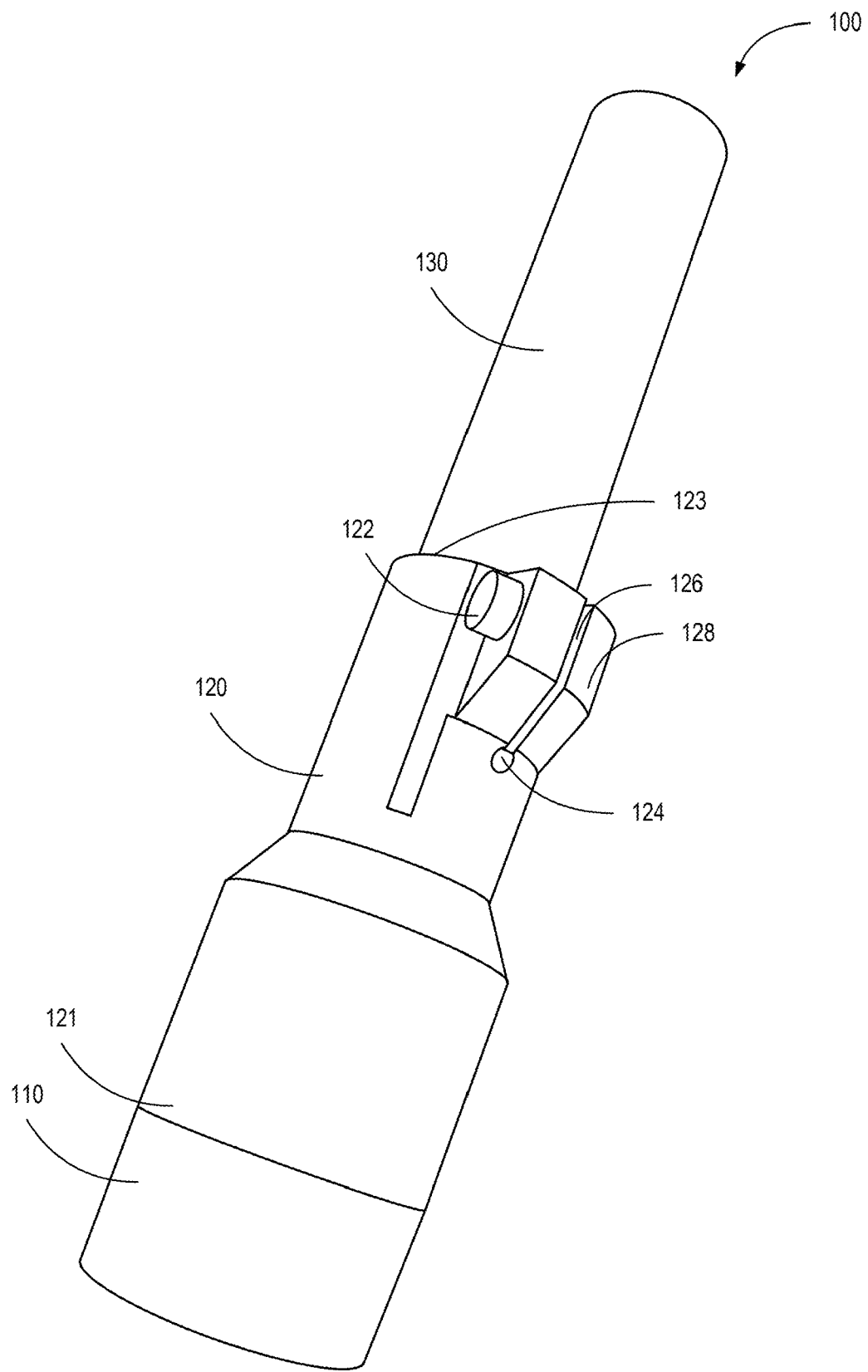
FIG. 1 is a perspective view of a non-snag prosthetic foot, according to one embodiment.

This disclosure describes a low-cost prosthetic foot for use with a leg prosthesis. The prosthetic foot described herein is referred to as a non-snag prosthetic foot, and may be used to replace or supplement an amputee's current prosthetic foot to limit catching on environmental obstacles.

A basic prosthetic foot does not articulate and therefore poorly mimics ankle action. This results in a number of undesirable traits. For instance, a non-articulating foot may drag the toe while walking and snag on environmental obstacles such as long grass, brush, or roots. Additionally, the non-articulating foot may get caught under overhanging structures. For example, the non-articulating foot may get caught under a kitchen counter or a pedal of a car.

To overcome some of these issues, one or more joint axes may be added. A single-axis joint may allow a prosthetic foot to articulate up and down. Even this single-axis movement may benefit an amputee. For example, a single-axis prosthetic foot may articulate when an amputee moves the foot from under a kitchen counter preventing it from catching. However, these joints will not lift automatically while walking. Thus, a single- or multi-axis foot may drag its toe just like the basic prosthetic foot and potentially snag on environmental obstacles. Additionally, each axis adds weight to the prosthesis, requires periodic servicing, and is more expensive than the basic prosthetic foot.

Additional elements can make a prosthetic foot more dynamic, responsive, and stable. These additional elements may cause the prosthetic foot to more closely mimic the movement of a human foot. For example, a dynamic-response foot may mimic the inversion and eversion movements of a human ankle. A microprocessor-controlled (MPC) foot introduces computer-controlled sensors to adjust the prosthetic foot. While these elements may make the prosthetic foot more closely mimic a human foot, each element adds significant cost and introduces additional maintenance.

Using these and other components, prosthetic feet have been designed for various activities. For example, prosthetic feet have been designed for walking, running, cycling, swimming, or skiing. Each of these specialized feet features components that make the prosthetic foot more suited for that activity. However, as described above, these specialized feet add expense and introduce maintenance issues.

Many amputees are prevented from participating in activities they were passionate about because they are faced with the expense of a specialized prosthetic foot or the limitations of a basic prosthetic foot. Embodiments of the non-snag prosthetic foot described herein may economically allow an amputee to participate in activities for which a basic prosthetic foot would function poorly. For example, the non-snag prosthetic foot may facilitate hunting, fishing, or hiking in locations where dense vegetation may snag a basic prosthetic foot and cause the amputee to trip. Embodiments of the non-snag prosthetic foot may comprise low-cost components and can thus be manufactured inexpensively.

The phrase "coupled to" is broad enough to refer to any suitable coupling or other form of interaction between two or more entities. Thus, two components may be coupled to each other even though they are not in direct contact with each other.

The terms "proximal" and "distal" are opposite directional terms. As used herein, the distal end of a prosthetic foot or component is the end of the component that is furthest from a user during ordinary use. The proximal end refers to the opposite end, or the end nearest the user during ordinary use. For example, the proximal end of a prosthetic foot couples to a prosthesis pylon during use, while the distal end is used to strike the ground.

Embodiments may be understood by reference to the drawings, wherein like parts are designated by like numerals throughout. The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

FIG. 1 is a perspective view of a non-snag prosthetic foot 100, according to one embodiment. The non-snag prosthetic foot 100 comprises a wear member 110 and a cuff 120.

The wear member 110 is configured to strike the ground when a user walks with the non-snag prosthetic foot 100. In some embodiments, the wear member 110 is made of an elastomer. For example, the wear member 110 may be made of rubber, plastic, nylon, polycarbonate, and/or polystyrene. The materials forming the wear member 110 may be adjusted to change the hardness of the wear member 110. For example, a user may prefer a soft material to absorb the shock from walking, or a harder material may be used to increase longevity of the wear member 110.

In some embodiments, a combination of materials may be used. For example, a lower portion of the wear member 110 may be a hard material, and an upper portion of the wear member 110 may be a soft material. In some embodiments, a high-friction lower portion may provide greater traction for a user. In this way, the wear member 110 may take advantage of the characteristics of multiple materials.

The shape of the wear member 110 may prevent the non-snag prosthetic foot 100 from getting caught on obstacles. For example, as shown, the wear member 110 may be cylindrical. The cylindrical shape has no protrusions, edges, or corners for obstacles to catch. In some embodiments, the wear member 110 may be oblong shaped or polygon shaped.

The wear member 110 may be rotatable to allow a user to alter an orientation of the symmetric wear member 110. The rotation of the wear member 110 may facilitate even wearing of the wear member 110. For example, if a user pronates the non-snag prosthetic foot 100 as part of his or her natural stride, an inner bottom edge of the wear member 110 may wear faster than other portions of the wear member 110. If the inner bottom edge is allowed to wear much faster than other portions of the wear member 110, the non-snag prosthetic foot 100 may become over-pronated, which may reduce comfort and cause injuries. If a user notices uneven wear, rotating the wear member 110 may facilitate correction to the stride of the user. Thus, the wear member 110 may be rotatable to facilitate even wear and increase the comfort of the user.

The wear member 110 may be symmetrical. The symmetry of the wear member 110 may allow the wear member 110 to provide the same support when the wear member 110 is rotated. For example, as shown, the wear member 110 may have radial symmetry allowing the wear member 110 to be rotated to various positions while maintaining alignment with the cuff 120 for even wear. In some embodiments, the wear member 110 may have bilateral symmetry limiting the rotation of the wear member 110 to a first and a second position while maintaining alignment with the cuff 120.

The cuff 120 may include a distal end 121 with a mating feature (e.g., threaded interface 322 of FIG. 3) to couple to the wear member 110, and a proximal end 123 with a receptacle (e.g., receptacle 324 of FIG. 3) with an opening having an adjustable diameter.

The proximal end 123 may include a slot 126 to allow the receptacle to be bent to adjust the diameter of the opening. The degree to which the opening may adjust may be proportional to the width of the slot 126. For example, if the slot 126 is wider, the opening will have a larger range of diameters when compared with a narrow slot 126. A pivot hole 124 may be drilled at the distal end of the slot 126. The pivot hole 124 may provide a point at which sides of the slot 126 may pivot. The pivot hole 124 may also assist in defining an end of the slot 126 during manufacturing.

The opening of the cuff 120 may be reduced or enlarged using a bolt 122 near the proximal end of the cuff 120. The bolt 122 may extend through a protrusion 128 that is divided by the slot 126. The bolt 122 may couple to the protrusion 128 on both sides of the slot 126. The bolt 122 may be perpendicular to a major axis of the slot 126 and a longitudinal axis of the cuff 120. Further, the bolt 122 may be parallel with the opening of the receptacle. If the bolt 122 is tightened, the bolt 122 applies a compression force that causes the slot 126 to be reduced, thereby reducing the overall diameter of the opening. If the bolt 122 is loosened, the compression force is reduced and a tensile force of the material of the cuff 120 may cause the diameter of the opening to enlarge.

The cuff 120 may receive a prosthesis pylon 130 in the receptacle. The cuff 120 may selectively retain the prosthesis pylon 130 by adjusting the diameter of the opening. For example, a user may insert the prosthesis pylon 130 into the cuff 120, and thread the bolt 122 into the cuff 120, causing the opening of the cuff 120 to be reduced. The reduced opening causes a friction fit between the prosthesis pylon 130 and the cuff 120. The friction fit may prevent the prosthesis pylon 130 from slipping or being removed from the cuff 120 during use.

Figure 2:
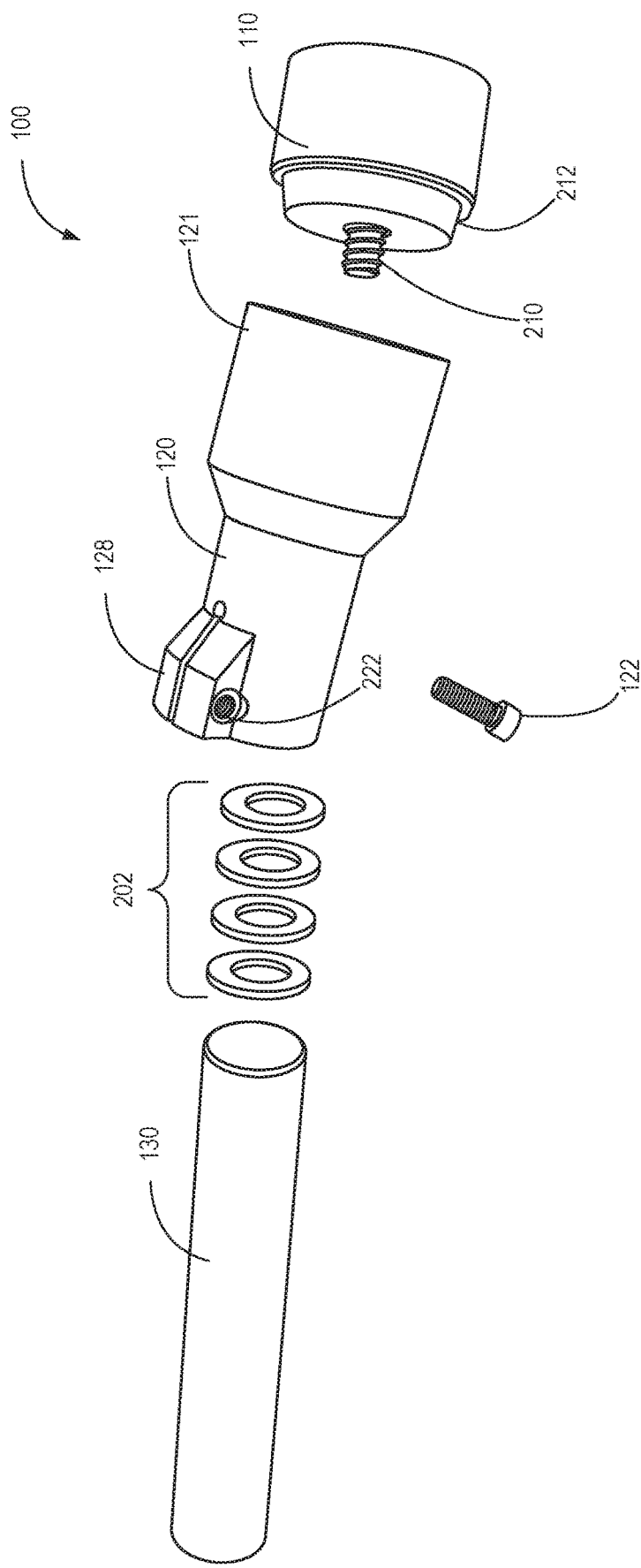
FIG. 2 is an exploded view of the non-snag prosthetic foot of FIG. 1.

FIG. 2 is an exploded view of the non-snag prosthetic foot 100 of FIG. 1. In some embodiments, the wear member 110 may be threaded onto the distal end 121 of the cuff 120, and the prosthesis pylon 130 may be slid into the proximal end 123 of the cuff 120.

The wear member 110 may include a mating feature to couple the wear member 110 to the cuff 120. In the illustrated embodiment, the mating feature comprises a bolt 210. A corresponding threaded hole may be included on the cuff 120. While the illustrated embodiment has a bolt 210 protruding from the proximal end 212 of the wear member 110, in some embodiments, the proximal end 212 may include threads that may be used for coupling. In other embodiments the mating feature may include hardware that mechanically joins two objects together. For example, the mating feature may include a peg, clamp, latch, pin, lock, magnet, and/or clip.

In some embodiments, the mating feature facilitates rotation of the symmetric wear member 110 for even wear. For example, the illustrated bolt 210 couples the wear member 110 to the cuff 120 with a longer thread than necessary. The extended thread may allow the wear member 110 to stay coupled to the cuff 120 through at least one full rotation. Thus, the extended thread of the bolt 210 may allow the wear member 110 to rotate 360 degrees while staying attached to the cuff 120.

The wear member 110 may include a tapered proximal end 212 that seats in the cuff 120. In some embodiments, the tapered proximal end 212 provides frictional engagement with the cuff 120 to prevent the wear member 110 from unintentionally rotating. In some embodiments, the tapered proximal end 212 may include a high-friction surface to limit unintentional rotation.

A user may remove and replace the wear member 110 from the non-snag prosthetic foot 100 of FIG. 1. This may allow a user to select a different wear member 110. In some embodiments, the non-snag prosthetic foot 100 may include a plurality of replacement wear members with various degrees of hardness. The various replacement wear members may accommodate different user preferences.

The bolt 122 may thread into a bolt hole 222 with internal threads on the protrusion 128. In other embodiments, the bolt 122 may couple to an external nut without the need for the internal threads. In some embodiments, tightening the bolt 122 causes a width of the slot 126 to reduce and thereby makes the diameter of the opening of the cuff 120 smaller.

A vertical adjustment mechanism 202 may selectively alter a depth of the receptacle of the cuff 120 to vertically displace the prosthesis pylon 130. In the illustrated embodiment, the vertical adjustment mechanism 202 is a plurality of spacers. One or more of the spacers may be selectively inserted in the receptacle to incrementally adjust the height of a prosthetic leg. Each spacer may be hollow to reduce weight.

Figure 3:
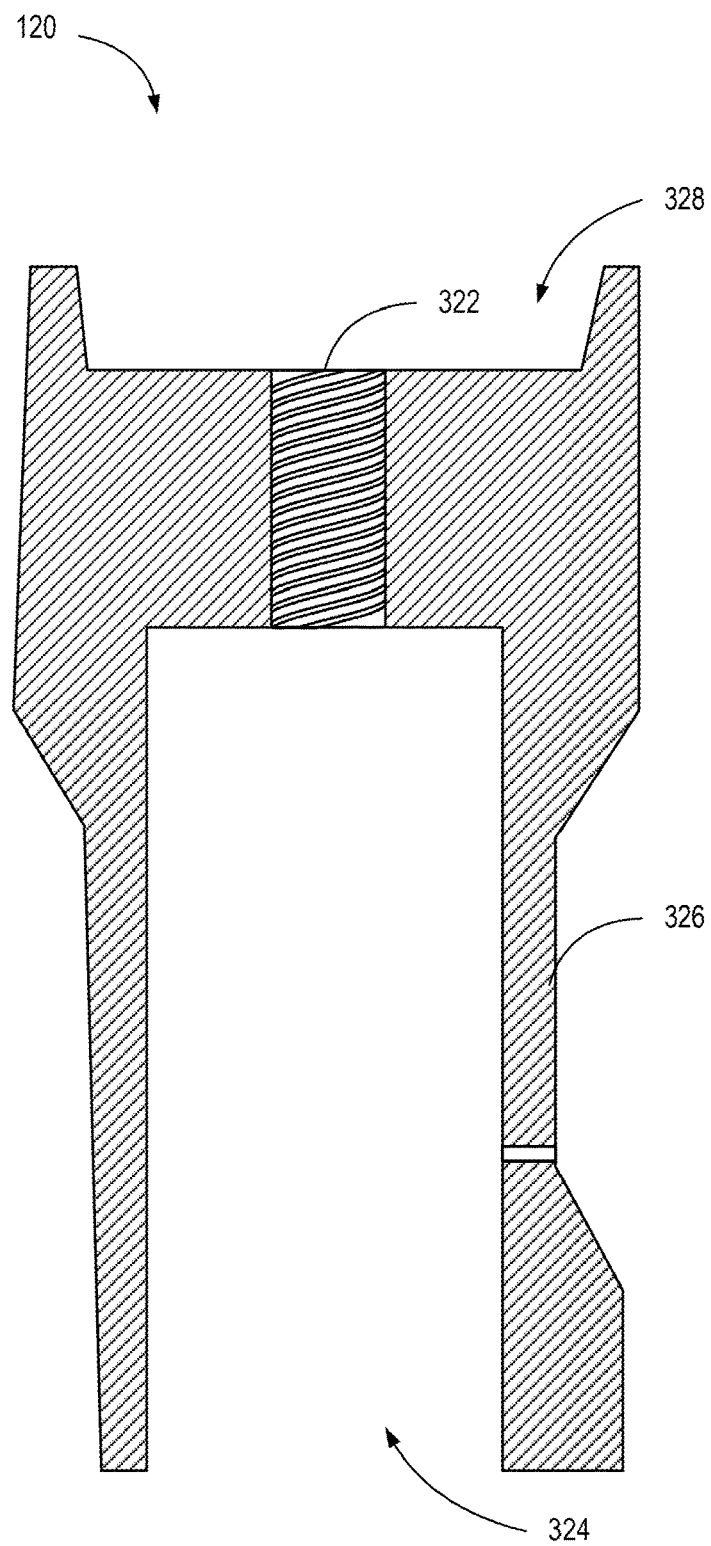
FIG. 3 is a cross-sectional view of a cuff of the non-snag prosthetic foot of FIG. 1.

FIG. 3 is a cross-sectional view of the cuff 120 of the non-snag prosthetic foot 100 of FIG. 1. The cuff 120 couples to the wear member and the prosthesis pylon. The wear member and the prosthesis pylon may have different mating features. Thus, the cuff 120 adapts the interface of the wear member to the prosthesis pylon.

The cuff 120 may include a receptacle 324 to receive and couple to the prosthesis pylon. The receptacle 324 is sized and shaped to receive a prosthesis pylon. For instance, as shown, the receptacle 324 may include a single cylindrical chamber to house a cylindrical prosthesis pylon. The shape of the receptacle 324 may be altered to receive different shaped prosthesis pylons. In some embodiments, the chamber may taper to provide a frictional fit with a prosthesis pylon near a distal end of the chamber.

The receptacle 324 may selectively retain a prosthesis pylon by adjusting a diameter of a chamber opening. As discussed previously, a bolt may provide a compression force across a slot to reduce the diameter of the chamber opening. The reduced diameter may restrict movement of a prosthesis pylon inserted in the chamber. Chamber walls 326 of the receptacle 324 may have sufficient tensile strength that when the compression force is relieved, the chamber opening returns to an original shape.

The cuff 120 may also include a mating feature 322 to couple with a wear member. The mating feature 322 may have a helical thread to couple the wear member to the cuff 120 with a rotational movement. As shown, the mating feature 322 may extend to the distal end of the receptacle 324.

In some embodiments, the corresponding mating feature of the wear member may be used to adjust a height of the prosthetic leg. For example, the corresponding mating feature of the wear member may extend through the mating feature 322 of the cuff 120 to the distal end of the receptacle 324. Rotational movement of the wear member may cause the corresponding mating feature of the wear member to linearly displace a floor of the receptacle 324 at the distal end. In some embodiments, the corresponding mating feature may be used in combination with spacers to precisely adjust the height of the prosthetic leg. For example, the spacers may provide larger graduated changes to height while the corresponding mating feature may provide smaller, more incremental adjustments.

The cuff 120 may further include an inset seat 328 to receive a proximal portion of the wear member. The inset seat 328 may be sized and shaped to fit the proximal portion of the wear member. The inset seat 328 may frictionally engage the proximal portion of the wear member.

References to approximations are made throughout this specification, such as by use of the term "near." For each such reference, it is to be understood that, in some embodiments, the value, feature, or characteristic may be specified without approximation. For example, where qualifiers such as "near" and "approximately" are used, these terms include within their scope the qualified words in the absence of their qualifiers. For example, where the term "approximately aligned" is recited with respect to a feature, it is understood that in further embodiments, the feature can have a precisely aligned configuration.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A prosthetic foot comprising:
 a symmetric wear member that is rotatable to allow a user to alter an orientation of the symmetric wear member for even wear;
 a cuff comprising a distal end and a proximal end, the distal end comprising a mating feature to couple to the symmetric wear member, the proximal end comprising a receptacle with an opening having an adjustable diameter,
  wherein the receptacle is sized and shaped to receive a prosthesis pylon and selectively retains the prosthesis pylon; and
 a vertical adjustment mechanism that selectively alters a depth of the receptacle of the cuff to vertically displace the prosthesis pylon, wherein the vertical adjustment mechanism comprises a plurality of spacers that are each removable and insertable in the receptacle beneath the prosthesis pylon to adjust a height of the prosthesis pylon, wherein each spacer placed in the receptacle incrementally displaces the prosthesis pylon.

2. The prosthetic foot of claim 1, wherein the symmetric wear member is made of an elastomer.

3. The prosthetic foot of claim 1, wherein the prosthesis pylon selectively retains by adjusting the diameter of the opening.

4. The prosthetic foot of claim 1, wherein the symmetric wear member is replaceable.

5. The prosthetic foot of claim 1, further comprising a plurality of replacement wear members, wherein the plurality of replacement wear members have various degrees of hardness.

6. The prosthetic foot of claim 1, wherein the mating feature facilitates rotation of the symmetric wear member.

7. The prosthetic foot of claim 6, wherein the mating feature comprises a threaded hole, and the symmetric wear member comprises a bolt to screw into the threaded hole.

8. The prosthetic foot of claim 1, wherein the symmetric wear member comprises a tapered proximal end that seats in the cuff.

9. The prosthetic foot of claim 8, wherein the tapered proximal end provides frictional engagement with the cuff to prevent the symmetric wear member from unintentionally rotating.

10. The prosthetic foot of claim 1, wherein the proximal end of the cuff further comprises a slot to allow the receptacle to be bent to adjust the diameter of the opening.

11. The prosthetic foot of claim 10, further comprising:
a bolt to adjust the diameter of the opening of the receptacle,
wherein the cuff further comprises a protrusion divided by the slot, the protrusion comprising a threaded interface that couples with the bolt,
wherein tightening the bolt causes a width of the slot to reduce and thereby makes the diameter of the opening of the receptacle smaller.

12. The prosthetic foot of claim 1, wherein the symmetric wear member comprises a single central bolt; and
wherein the mating feature comprises a threaded hole corresponding to the single central bolt, wherein the symmetric wear member is rotatable while remaining coupled to the cuff by rotating the single central bolt within the threaded hole.

13. A prosthetic leg comprising:
a leg socket to receive a limb of a user;
a prosthesis pylon coupled to the leg socket; and
a prosthetic foot comprising:
a symmetric wear member that is rotatable to allow the user to alter an orientation of the symmetric wear member for even wear;
a cuff comprising a distal end and a proximal end, the distal end comprising a mating feature to couple to the symmetric wear member, the proximal end comprising a receptacle with an opening having an adjustable diameter,
wherein the receptacle is sized and shaped to receive the prosthesis pylon and selectively retains the prosthesis pylon by adjusting the diameter of the opening; and
a vertical adjustment mechanism that selectively adjusts a depth of the receptacle of the cuff to vertically displace the prosthesis pylon and alter a height of the prosthetic leg, wherein the vertical adjustment mechanism comprises a plurality of spacers that are each removable and insertable in the receptacle beneath the prosthesis pylon to adjust a height of the prosthesis pylon, wherein each spacer placed in the receptacle incrementally displaces the prosthesis pylon.

14. The prosthetic leg of claim 13, wherein the symmetric wear member is made of an elastomer.

15. The prosthetic leg of claim 13, wherein the symmetric wear member is made of a material selected from a group consisting of rubber, plastic, nylon, polycarbonate, and polystyrene.

16. The prosthetic leg of claim 13, wherein the symmetric wear member is replaceable.

17. The prosthetic leg of claim 13, further comprising a plurality of replacement wear members wherein the plurality of replacement wear members have various degrees of hardness.

18. The prosthetic leg of claim 13, wherein the mating feature facilitates rotation of the symmetric wear member.

19. The prosthetic leg of claim 18, wherein the mating feature comprises a threaded hole, and the symmetric wear member comprises a bolt to screw into the threaded hole.

20. The prosthetic leg of claim 13, wherein the symmetric wear member comprises a single central bolt; and
wherein the mating feature comprises a threaded hole corresponding to the single central bolt, wherein the symmetric wear member is rotatable while remaining coupled to the cuff by rotating the single central bolt within the threaded hole.

* * * * *